United States Patent
Shimizu et al.

(10) Patent No.: US 6,271,350 B1
(45) Date of Patent: Aug. 7, 2001

(54) FISH COLLAGEN AND METHOD OF PRODUCING SAME

(75) Inventors: Johsuke Shimizu; Hideki Shimizu; Koji Nagashima, all of Ebetsu; Kunishige Yamada; Minori Takamatsu, both of Rumoi, all of (JP)

(73) Assignees: Thara & Company Ltd.; Hokkaido Government, both of Hokkaido (JP)

( * ) Notice: Subject to any disclaimer, the term of this patent is extended or adjusted under 35 U.S.C. 154(b) by 0 days.

(21) Appl. No.: 09/357,908

(22) Filed: Jul. 21, 1999

(30) Foreign Application Priority Data

Aug. 11, 1998 (JP) .................................................. 10-239584

(51) Int. Cl.$^7$ .................................................. C07K 14/78
(52) U.S. Cl. .............................................................. 530/356
(58) Field of Search ..................... 530/356, 422, 530/423, 427; 426/656, 657; 514/21; 623/15, 15.12; 602/50

(56) References Cited

U.S. PATENT DOCUMENTS 5,420,248  *  5/1995   Devictor et al. ..................... 530/356
5,698,228  * 12/1997   Takai et al. .......................... 424/549

FOREIGN PATENT DOCUMENTS 5-155900  *  6/1993  (JP) .
 910246       1/1997  (JP) .

OTHER PUBLICATIONS

Montero et al. Effect of pH and the Presence of NaCl . . . J. Sci. Food Agric. vol. 54, pp. 137–146, 1991.*

* cited by examiner

Primary Examiner—Jeffrey E. Russel
(74) Attorney, Agent, or Firm—Browdy and Neimark

(57) ABSTRACT

A collagen is extracted and produced from a raw fish skin through the steps: a salt admixing step for admixing a salt (e.g. NaCl, KCl or the like) with a raw fish skin so as to allow non-collagen substances or portions (including fats and other tissue portions than a collagen portion) to be removed from the fish skin, while simultaneously degreasing and deodorizing the skin under the salt effect; a salt removal step for causing the admixed salt and non-collagen substances or portions to remove from the skin, achieving the fats removal and deodorization; a collagen extraction step for extracting a collagen (gelatinous) from the thustreated skin; and a filtration step for filtering and refining the extracted collagen so as to obtain a refined collagen. The refined collagen may be dried and solidified. Thus, since the inexpensive salt is used for effective removal of non-collagen substances or portions to obtain a collagen portion, the method itself is simplified and economical. Further, the fish collagen obtained thereby, be it fluid or dried, is of a highly refined property, i.e. colorless, odorless and degreased, which is suited for food product elements and various industrial uses.

13 Claims, No Drawings

FISH COLLAGEN AND METHOD OF PRODUCING SAME

BACKGROUND OF INVENTION

1. Field of the Invention

The present invention relates to a collagen obtained from fishes and a method of producing such fish collagen. In particular, the present invention is directed to a collagen obtainable from the skin of fishes and a method of extracting and producing the same.

2. Description of Prior Art

A great amount of waste portions of fishes, which are generally considered useless or untapped, had been discarded. This has been one of the major problems that we should address in the modem society to find various ways to use that seemingly unserviceable portion of fishes in many applicable fields. One of the typical waste examples is a skin of fishes, particularly the skins of salmons and trouts.

The salmon and trout skins contain collagen as a principal ingredient. Until recently, such collagen has been deemed a useless portion of fishes and no one had ever contemplated upon adapting the fish skin collagen for various uses and applications. In the past, nearly ten thousand salmon and trout skins had been wasted and discarded in vain.

In view of collagen being obtained from mammals and widely available as an edible material, researches are now being made about fish collagen and in particular about salmon and trout skins, in which a collagen is a main ingredient of the tissues. Recent years, thus, have seen some methods proposed to extract and produce a collagen from fish skins, including the skins of salmon and trout in question.

The fish skin collagen, however, differs in characteristics from mammalian collagen and requires relatively troublesome extraction steps involving deodorization, decolorization and degreasing of the skin. Also, the extracted collagen may hardly be refined to a satisfied degree. Those points of concern have yet to be solved in assuring that the collagen is edible.

Hitherto extracting and producing of fish skin collagen entails use of an organic solvent, such as ethanol, to remove non-collagen substances or portions, i.e. other substances and portions than the collagen, including proteins, fats and oils, from the fish skin. More or less, the process leaves some substances, particularly fats and oils, in the fish skin until the collagen is extracted. Ethanol is used to remove the residual fats or non-collagen substances or portions from the skin. Namely, the fish skin is placed in the ethanol solution and washed by stirring therein for that removal purpose.

However, this sort of conventional method is found defective in that, after the removal of non-collagen substances or portions by ethanol, much care is required not only to insure washing off the ethanol from the skin in water to avoid its chemical influence on the skin, but also to treat the waste water thereafter so as to allow a cleaned waste water to be drained out. Further, defective is this method in requiring a quite expensive distillation system to recover the ethanol used in that fat and non-collagen substance removal process. As a result, the production of fish skin collagen has been considered extremely high in costs.

SUMMARY OF THE INVENTION

With the above-stated drawbacks in view, it is therefore a primary purpose of the present invention to provide a simplified and economical method of extracting and producing a collagen from fish skin and also to provide a highly refined fish collagen obtained thereby.

To achieve that purpose, in accordance with the present invention, there are basically provided the following steps:

step of providing a raw skin of the fish;

salt admixing step of admixing a salt with said raw fish skin and then leaving the raw fish skin mixed with the salt in a cold condition for degreasing and deodorization thereof;

salt removal step of removing the salt from the raw fish skin that has undergone the salt admixing step, together with non-collagen substances or portions, so that a desalted portion of the raw fish skin is collected;

collagen extraction step of extracting a collagen portion from that desalted portion of raw fish skin; and filtration step of filtrating said collagen portion so as to remove residual non-collagen substances, including fats, oils, odor and colors, therefrom, thereby obtaining a refined collagen.

Accordingly, non-collagen substances and portions are effectively and easily removed from the fish skin, using an inexpensive salt, to collect a collagen portion, and further, the collagen portion is filtered into a highly purified collagen (fluid) suited for food product elements and for various industrial uses, including medical and cosmetic materials and emulsifier for photographic films.

The salt usable in the present invention includes NaCl, KCl, $Na_2SO_4$ and the like.

In one aspect of the present invention, after having washed the raw fish skin, the salt admixing step includes admixing the salt with the raw fish skin in an amount equal to that of the latter and then leaving the raw fish skin thus mixed with the salt in a cold condition below a room temperature. Or, the salt may be admixed with the raw fish skin an amount 0.2 to 3 times that of the latter.

Preferably, the salt removal step may include the step of applying a filtration means to the raw fish skin mixed with the salt and washing the same in water stream to remove the salt therefrom together with the non-collagen substances or portions via the filtration means, whereby the desalted portion of the raw fish skin is collected in the filtration means.

Preferably, the collagen extraction step may include immersing and incubating the raw fish skin in hot distilled water of 70 to 90° C. to thereby extract the collagen portion therefrom.

In another aspect of the invention, as the collagen portion extracted at the collagen extraction step is an impure collagen solution which still contains impurities, the filtration step may include providing 1 W/V % of activated carbon with respect to an amount of the impure collagen solution, adding such 1W/V % of activated carbon to the solution, then stirring both of those activated carbon and impure collagen solution for a predetermined period of time, and after lapse of a predetermined period of time, subjecting a fluid mixture of the activated carbon and impure collagen solution to suction filtration using a pulp for filtration, cerite and kieselguhr for one hour, thereby filtering out impurities from the impure collagen solution to obtain a refined fluid collagen. A fish collagen thus obtained is a highly refined fluid collagen suited for food and industrial uses.

In yet another aspect of the invention, the above-described method further includes a drying step of drying and solidifying the refined collagen obtained at the filtration step, so as to provide a solidified collagen. The solidified collagen may be broken into fine powders. The collagen powders are also suited for food and industrial uses. At this step, preferably, hot air of 70° C. may be applied to the refined collagen for 12 hours so as to obtain at least one bar of solidified collagen.

All other specific features and advantages of the present invention will become apparent from reading of the descriptions below.

DETAILED DESCRIPTION OF PREFERRED EMBODIMENT OF THE INVENTION

Hereinafter, one example of fish skin collagen and method for extracting and producing the same will be described in detail.

In the present embodiment, a raw skin of salmon is, by way of example, used as a raw material for producing a collagen. Of course, the salmon skin is not limitative, but any other raw skins of fishes including trout, walleye pollack, shark, Atka mackerel and halibuts, may be used.

In accordance with this mode of the present invention, in summary, a fish collagen is extracted and produced by removing non-collagen substances or portions from a raw fish skin through the following generic steps: a salt admixing step for admixing a salt (e.g. NaCl, KCl or the like) with a raw fish skin so as to allow non-collagen substances or portions (including fats and other tissue portions than a collagen portion) to be removed from the fish skin, while simultaneously degreasing and deodorizing the skin under the salt effect; a salt removal step for causing the salt and non-collagen substances or portions (bonded with the salt) to remove from the skin, achieving the fats removal and deodorization; a collagen extraction step for extracting a collagen (gelatinous or fluid) from the thus-treated skin; a filtration step for filtering and refining the extracted collagen to obtain a refined collagen; and a drying step for drying and solidifying the refined collagen.

First of all, the salt admixing step will be described as follows.

At this step, a salmon skin, which has been peeled from the body of salmon, is washed well in water (tap water) to remove scales, fats and partial flesh from the skin. Then, the washed skin is cut into small pieces. Preferably, the skin should be cut square by 5 cm or by a proper small dimensions to facilitate the salt admixing processes to be specified below.

The properly cut small pieces of salmon skins should be drained of the residual water thereon to place them in a condition ready for mixing with a salt. In this embodiment, NaCl is employed as an example of one of the salts usable in the present invention. An amount of NaCl equal to a total amount of the salmon skin pieces may be admixed therewith so well that all the skin pieces are evenly covered with NaCl.

In this regard, it is desirable that NaCl be admixed with the skin pieces in an amount 0.2 to 3 times a total amount of the latter with the view to promoting removal of non-collagen substances or portions therefrom. It is however important that the amount of NaCl be maintained within such mixing ratio relative to that of skin pieces. For, experiments show that a small mixing ratio of NaCl below the 0.2 value results in decreasing the efficiency of removal of non-collagen substances from fish skins, whereas an excessive mixing ratio of NaCl over the 3 value is found to remove the collagen as well from the fish skins.

The salmon skin pieces thus mixed with NaCl are left cold for about one week at the temperature of 4° C. This temperature is not limited to 4° C., but may be set at an appropriate degree lower than ambient or room temperature.

According to our experiments, leaving the salted skin pieces in a cold condition below a room temperature for about one week increases the mixing efficiency of NaCl with the salmon skin pieces as well as the rate of non-collagen substances removal from the skin pieces. Those conditions are also found effective in making positive the NaCl's deodorizing and degreasing actions on fish skins.

Salt usable at this process may include potassium chloride (KCl), sodium sulfate ($Na_2SO_4$) or the like, instead of NaCl, insofar as they effectively assist in extracting a collagen from fish skin. It is noted that the salts, including NaCl, within the gist of the present invention, have a property for chemical bonding with the non-collagen substances or portions in the fish skin, excepting a collagen, by virtue of which, only the non-collagen substances or portions are made decomposable, allowing for easy separation of a collagen portion therefrom. Hence, in accordance with the present invention, admixing of the salt(s) with the fish skin is of an inventive significance for easy, inexpensive extraction of collagen.

It is also appreciated that the NaCl used is, among other salts, the least expensive salt available for removing the non-collagen substances or portions from fish skin, which will substantively save costs and charges incurred in the collagen production.

After the completion of about one-week salting down of salmon skin pieces stated above, the salted skin pieces are subjected to salt removal. Description will now be made of the salt removal step. At this stage, the salted skin pieces are closely enclosed with a filtration cloth. Then, the filtration cloth containing the salted skin pieces is exposed to a stream of water and washed well therein for about 30 minutes to 1 hour, causing thereby most of non-collagen substances or portions to decompose into minute pieces and escape out through the fine meshes of cloth, whereby collagen portions of the skin pieces are caught by the meshes against leakage therethrough. It is to be understood that this washing in water stream easily removes the water-soluble NaCl almost completely from the skin pieces, and at the same time, allows an appreciable amount of non-collagen substances or portions to be removed together with the NaCl from the skin pieces. With this washing filtration, the desalted portions of skin pieces remained in the cloth contain a collagen. In place of the filtration cloth, a piece of gauze or any other suitable filtration means having fine meshes may be utilized for that purpose.

The time required for washing away the salt and non-collagen portions at this stage is not limited to the afore-said range, but dependent upon the circumstances and conditions where a worker can recognize termination of removal of those elements from the skin pieces and a timing for stopping the washing in water stream. In other words, the time depends on a time which the worker will take to determine, with his or her eyes, that the portions of skin pieces, decomposable after the salt admixing step, are cleared away from the skin pieces left in the filtration cloth.

It is seen that the foregoing series of salt admixing and removal steps provide degreasing and deodorization of the salmon skin pieces as well as removal of non-collagen substances or portions therefrom.

Next, the thus-treated salmon skin pieces (i.e. desalted portions of the salmon skin pieces) are subjected to extraction of collagen. At this step, first, the residual water on the skin pieces is wiped off well. Thereafter, the pieces are immersed in distilled water heated at 80° C. and incubated therein for two hours under the same 80° C. temperature.

After lapse of two hours, it is observed that a gelatinous collagen (i.e. a thermally denatured collagen) is eluted from the skin pieces in the heated water. Note that 80° C. degree of hot distilled water is optimum for good gelation and gel strength of collagen extracted therein. The temperature of distilled water is not restricted thereto, but may be set within the range of 70 to 90° C. In this regard, however, adjusting the temperature out of that range, i.e. either lower than 70° C. or higher than 90° C., will adversely affect the gelation and gel strength of collagen (thermally denatured collagen), with the high likelihood that a poor denaturing and degradation of collagen will occur and limit its use in both food and industrial fields, including food product elements, medical and cosmetic materials, and emulsifier for photographic films. In accordance with the present invention, the use of hot distilled water is one of the effective factors for refining the collagen to a high purity degree.

The gelatinous collagen extracted at this point (thermally denatured collagen) still contains some large impurities such as scales and remaining non-collagen substances (fats and flesh parts, etc.). A filtration cloth is then used to filter the large impurities out from the gelatinous collagen.

It is desirable, at this extraction stage, that the quantity of distilled water be ten (10) times as much as that of the skin pieces treated by the aforementioned salt admixing and removal steps. This rate is found optimum in causing collagen to elute from the skin pieces in the hot water and be so properly denatured therein into a gelatinous form with a gel strength suited for the industrial and food product uses.

The next step is to finally filtrate and refine the thus-extracted gelatinous collagen (thermally denatured collagen) to a further purified degree for practical food and industrial uses. At this filtration step, there are basically provided the two filtration stages, one of them being an activated carbon based stirring filtration and the other being a suction filtration.

The activated carbon based stirring filtration will now be described.

The gelatinous collagen extracted at the foregoing step is in a liquid state or a rude solution containing the thermally denatured collagen with some impurities. Such impure collagen solution is subjected to a stirring filtration with an activated carbon. Namely, 1 W/V % of activated carbon is provided with respect to a quantity of the impure collagen solution, and added thereto. Then, the mixture of activated carbon and impure collagen solution is stirred by a stirrer for one hour, thereby absorbing some impurities from the solution. The mixture is still in the state of liquid or fluid.

Thereafter, such fluid mixture of activated carbon and collagen solution is subjected to the suction filtration. At this step, filter materials used comprise a pulp for filtration, cerite and kieselguhr. Specifically stated, the cerite and kieselguhr are admixed with the pulp in water to provide a filtration material. Then, the foregoing fluid mixture (activated carbon and collagen solution) is sucked and filtered via that filtered material by a sucking means (any suitable suction filter) so as to filter out most of impurities from the collagen solution. Preferably, this operation may be conducted once or twice. With the suction filtration, most of the non-collagen substances are removed from the extracted collagen, whereby a highly refined collagen is obtained, which is colorless (white) and odorless. Thus, this step finally removes residual fats, oils, odor and colors of other substances than the collagen, to assure the degreasing, deodorization and decolorization of the extracted collagen. It is appreciated that the highly refined collagen (fluid) is adaptable not only for use as an element of food products, but also for various industrial uses, such as for medical materials (e.g. hemostatic agent), cosmetic materials and emulsifier for photographic films.

Next, the refined collagen is subjected to drying to produce a solidified form of collagen. In the present mode, a hot-air blowing type of drying is employed for instance. Of course, this is not limiting, but any other ways of drying may be employed insofar as they meet the conditions stated below.

A recommended drying mode is such that hot air of 70° C. is applied by a hot air blower to the refined collagen for 12 hours, whereby one or more bars of solidified collagen are obtained, each containing not more than 2% water therein.

Finally, the collagen bars are broken by a pulverizer into fine powders so as to obtain collagen powder readily available in the commercial and industrial fields.

In accordance with the present invention, the collagen powders obtained has the following characteristics as compared with those of the conventional method using ethanol.

Note: The data given below is based on 1 kg of salmon skin.

|  | Conventional Method | The Present Invention |
| --- | --- | --- |
| Amount of gelatinous collagen recovered (rate) | 206.1 g (20.61%) | 213.0 g (21.30%) |
| Permeability rate | 81.2% | 80.7% |
| Melting point | 15.7 ° C. | 13.2 ° C. |
| Gel strength | 282.6 g | 266.3 g |
| Fats content | 0.297% | 0.309% |
| Ash content | 0.458% | 0.905% |
| Water content | 9.3% | 8.4% |
| Protein content | 97.8% | 95.6% |
| Tastes and flavor (organoleptic test) | good | excellent |
| Nasty smell (organoleptic test) | a little | none |

From the table above, it is seen that, in accordance with the method of the present invention, the collagen powders produced in the present invention are excellent in taste and flavor, and free of nasty smell, and that a gelatinous collagen can be recovered therefrom a greater amount than that of the conventional ethanol-based method. Thus, the collagen powders are reliable and widely applicable for various food products. Further, both of the fluid collagen refined by the suction filtration step and finally finished collagen powders are of a highly purified quality sufficient for various industrial uses, such as for the medical and cosmetic materials, and emulsifier for photographic films. In this connection, the collagen may be used for preparation of an artificial skin which will serve a replacement for bovine skin affected by mad cow disease.

Accordingly, in accordance with the present invention, the skin of fishes is used as a raw material for production of a collagen, and any other kinds of fishes, e.g. salmon, trout, walleye pollack, shark, Atka mackerel and halibuts may be used or that purpose. Since the raw fish skin is first mixed with a salt (one of salts including NaCl, KCl, etc.) and left in a cold condition, any chemical solvent such as ethanol is not required as in the prior art, and it is also possible to directly use salted fish skins available for the collagen production. In this context, the admixing of salt with the fish skins at the ratio of 0.2 to 3 relative thereto, as described earlier, permits for simply washing the salt away and does not require any recovery of the used salt, as opposed to the conventional method which inevitably needs the ethanol recovery. Thus, there is eliminated the necessity to use an expensive chemical solvent and expensive facilities for drainage and waste water treatment, which greatly improves the economy of collagen production. In addition, the salted fish skins can be stored for a long period of time and transferred to any destination, keeping their freshness. The salt per se is an inexpensive material effective in degreasing and deodorizing the raw fish skins, because it tends to be chemically bonded with most of non-collagen substances and portions in the fish skins. This also facilitates the ease of separation of a collagen portion from the non-collagen substances and portions at the subsequent salt removal step.

Moreover, obtaining a refined collagen, be it fluid or dried, is based on a series of the extraction step wherein the fish skins are immersed in a hot distilled water and the filtration step described above, hence simplifying the collagen extraction process itself.

It should be understood that the present invention is not limited to the modes and embodiments having been described so far, but any other modification, replacement and addition may be applied thereto without departing from the scopes of the appended claims.

What is claimed is:

1. A method for extracting and producing collagen from fish comprising:

providing raw fish skin;

admixing a salt with said raw fish skin and then leaving the raw fish skin mixed with the salt in a cold condition for degreasing and deodorization thereof;

apply the raw fish skin mixed with salt is applied to a filtration means and washing with water to remove the salt, whereby the desalted portion of the raw fish is collected in the filtration means;

extracting a collagen portion from said desalted raw fish skin; and filtering said collagen portion so as to remove residual non-collagen substances, including fats, oils, odor, and colors, therefrom, thereby obtaining a refined collagen.

2. The method according to claim 1, wherein said refined collagen is in a liquid or fluid state.

3. The method according to claim 1 wherein said fish is selected from the group consisting of salmon, trout, walleye pollack, shark, Atka mackerel, and halibut.

4. The method according to claim 1 wherein said salt is selected from the group consisting of sodium chloride, potassium chloride, and sodium sulfate.

5. The method according to claim 1 comprising, prior to said salt admixing step, washing the raw fish skin and cutting said raw fish skin into small pieces, thereby providing a plurality of small pieces of raw fish skin.

6. The method according to claim 1 wherein said raw fish skin is washed prior to said salt admixing step, and wherein said salt admixing step includes admixing the salt with the raw fish skin in an amount by volume equal to the volume of said raw fish skin, and then leaving said raw fish skin mixed with the salt at a temperature below room temperature.

7. The method according to claim 1 wherein said raw fish skin is washed prior to said salt admixing step, and wherein said salt admixing step includes admixing the salt with the raw fish skin in an amount by volume 0.2 to 3 times the volume of said raw fish skin, and then leaving said raw fish skin mixed with the salt at a temperature below room temperature.

8. The method according to claim 1 wherein said collagen extraction step includes immersing and incubating the desalted raw fish skin in water at a temperature of from 70 to 90° C. thereby to extract the collagen portion therefrom.

9. The method according to claim 8 wherein said water is distilled water heated to a temperature of 80° C. and wherein the raw fish skin is incubated in said distilled water for two hours.

10. The method according to claim 1 wherein said collagen portion extracted in said collagen extracting step is an impure collagen solution which still contains impurities, and wherein said filtration step includes providing 1 w/v % of activated carbon with respect to the impure collagen solution, and stirring both said activated carbon and impure collagen solution for a period of time; thereafter providing a fluid mixture of the activated carbon and impure collagen solution, and subjecting said fluid mixture of activated carbon and impure collagen solution to suction filtration for one hour using a pulp for filtration, cerite and kieselguhr, thereby filtering out impurities from the impure collagen solution to obtain a refined fluid collagen.

11. A method for extracting and producing collagen from fish comprising:

providing raw fish skin;

admixing a salt with said raw fish skin and leaving the raw fish skin mixed with the salt under cold conditions for degreasing and deodorization thereof;

removing salt and non-collagenous substances from said raw fish skin so that a desalted portion of the raw fish skin is collected;

extracting collagen from said desalted raw fish skin;

filtering said collagen to remove residual non-collagen substances including fats, oils, odor, and colors therefrom, thereby obtaining a refined collagen; and drying and solidifying said refined collagen.

12. The method according claim 11 wherein said drying includes applying air heated to 70° C. to said refined collagen for 12 hours, so as to obtain at least one bar of solidified collagen.

13. The method according to claim 12 wherein said at least one bar of collagen is broken into powdered form.

* * * * *

UNITED STATES PATENT AND TRADEMARK OFFICE
CERTIFICATE OF CORRECTION

PATENT NO. : 6,271,350 B1
DATED : August 7, 2001
INVENTOR(S) : Johsuke Shimizu et al.

It is certified that error appears in the above-identified patent and that said Letters Patent is hereby corrected as shown below:

<u>Title page,</u>
Item [73], Assignee, delete "Thara" and insert therefor -- Ihara--;

<u>Column 7,</u>
Line 34, delete "apply" and insert therefor -- applying --.

Signed and Sealed this

Sixteenth Day of July, 2002

*Attest:*

*Attesting Officer*

JAMES E. ROGAN
*Director of the United States Patent and Trademark Office*